(12) United States Patent
Ravi et al.

(10) Patent No.: US 10,815,216 B2
(45) Date of Patent: Oct. 27, 2020

(54) PROCESS FOR THE PREPARATION OF ARIPIPRAZOLE LAUROXIL

(71) Applicant: Neuland Pharma Research Private Limited, Hyderabad (IN)

(72) Inventors: Ponnaiah Ravi, Madurai (IN); Neela Praveen Kumar, Hyderabad (IN); Batthini Guruswamy, Hyderabad (IN); Krishnaiah Pendem, Hyderabad (IN); Satya Nagendra Kumar Lakkadasu, West Godavari District (IN); Mahesh Gattikoppula, Mahabubabad District (IN)

(73) Assignee: NEULAND PHARMA RESEARCH PRIVATE LIMITED, Hyderabad (IN)

( * ) Notice: Subject to any disclaimer, the term of this patent is extended or adjusted under 35 U.S.C. 154(b) by 0 days.

(21) Appl. No.: 16/469,259

(22) PCT Filed: Oct. 27, 2017

(86) PCT No.: PCT/IN2017/000125
§ 371 (c)(1),
(2) Date: Jun. 13, 2019

(87) PCT Pub. No.: WO2018/109775
PCT Pub. Date: Jun. 21, 2018

(65) Prior Publication Data
US 2020/0017463 A1 Jan. 16, 2020

(30) Foreign Application Priority Data
Dec. 14, 2016 (IN) .............................. 201641042604

(51) Int. Cl.
*C07D 401/12* (2006.01)
*C07D 215/227* (2006.01)

(52) U.S. Cl.
CPC ....... *C07D 401/12* (2013.01); *C07D 215/227* (2013.01)

(58) Field of Classification Search
CPC .............. C07D 215/227; C07D 401/12; A61K 31/496; A61K 47/14
USPC ........................................................ 544/363
See application file for complete search history.

(56) References Cited

U.S. PATENT DOCUMENTS

| 8,431,576 B2 * | 4/2013 | Remenar .............. C07D 215/22 514/249 |
| 9,193,685 B2 * | 11/2015 | Perry ........................ A61K 9/10 |
| 2014/0088115 A1 | 3/2014 | Perry et al. |

OTHER PUBLICATIONS

Leggio et al., RSC Adv., 2016, 6, 34468-34475.*
Weisz et al. Tetrahedron Letters, vol. 37, No. 5, 563-566, 1996.*
Husseini-Sarvari et al. IJST, A1, 7-11, 2012.*
Fife et al. Tetrahedron Letters, 27, 4933-4936, 1986.*
International Search Report for PCT Serial No. PCT/IN2017/000125 dated Oct. 1, 2018.

* cited by examiner

*Primary Examiner* — Venkataraman Balasubramanian
(74) *Attorney, Agent, or Firm* — McCormick, Paulding & Huber PLLC

(57) ABSTRACT

The present invention relates to an improved process for the preparation of Aripiprazole Lauroxil of Formula (I).

(I)

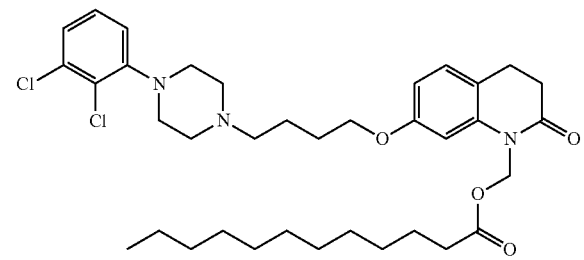

5 Claims, No Drawings

PROCESS FOR THE PREPARATION OF ARIPIPRAZOLE LAUROXIL

CROSS-REFERENCE TO RELATED APPLICATIONS

This application is a National Stage application of International Patent Application No. PCT/IN2017/000125, filed on Oct. 27, 2017, which claims priority to Indian Patent Application No. 201641042604 filed on Dec. 14, 2016, each of which is hereby incorporated by reference in its entirety.

TECHNICAL FIELD

The present invention relates to an improved process for the preparation of Aripiprazole Lauroxil of formula (I).

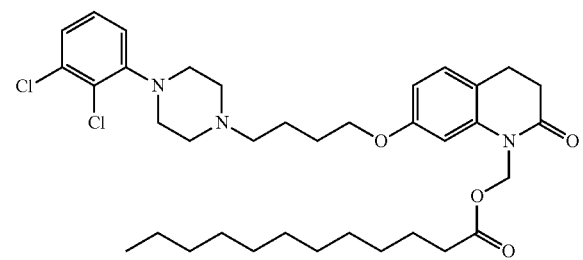

(I)

The present invention also relates to an improved process for the purification of Aripiprazole Lauroxil of formula (I).

BACKGROUND

Aripiprazole Lauroxil (ARISTADA®) is a prodrug of Aripiprazole. The chemical name of Aripiprazole Lauroxil is 7-{4-[4-(2,3-dichlorophenyl)-piperazin-1-yl]butoxy}-2-oxo-3,4-dihydro-2H-quinolin-1-yl)methyl dodecanoate. The empirical formula is $C_{36}H_{51}C_{12}N_3O_4$ and its molecular weight is 660.7 g/mol. The chemical structure is:

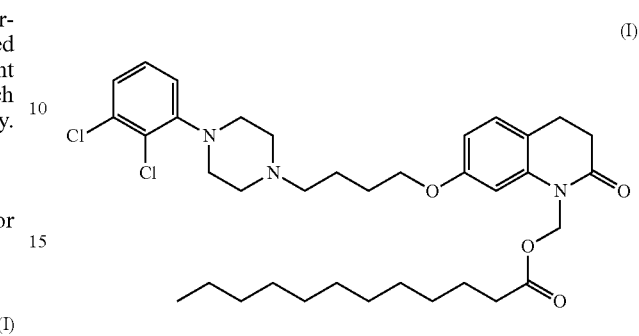

(I)

Aripiprazole Lauroxil is available as an extended-release injectable suspension and is a long-acting atypical antipsychotic that is approved by the U.S. Food and Drug Administration (FDA) for the treatment of schizophrenia. Aripiprazole Lauroxil is available in three dose strengths with once-monthly dosing and a six-week dosing option.

Aripiprazole Lauroxil was first described and claimed in U.S. Pat. No. 8,431,576. This patent describes a specific method for producing Aripiprazole Lauroxil by the reaction of Aripiprazole of formula (2) with formaldehyde in the presence of triethylamine and dimethylformamide to give N-hydroxymethyl aripiprazole of formula (3), which is then reacted with Lauric anhydride in tetrahydrofuran to give crude Aripiprazole Lauroxil of formula (I-1), followed by purification using chromatography to obtain pure Aripiprazole Lauroxil of formula (I). The above process is shown in the scheme-1 given below:

Scheme-1

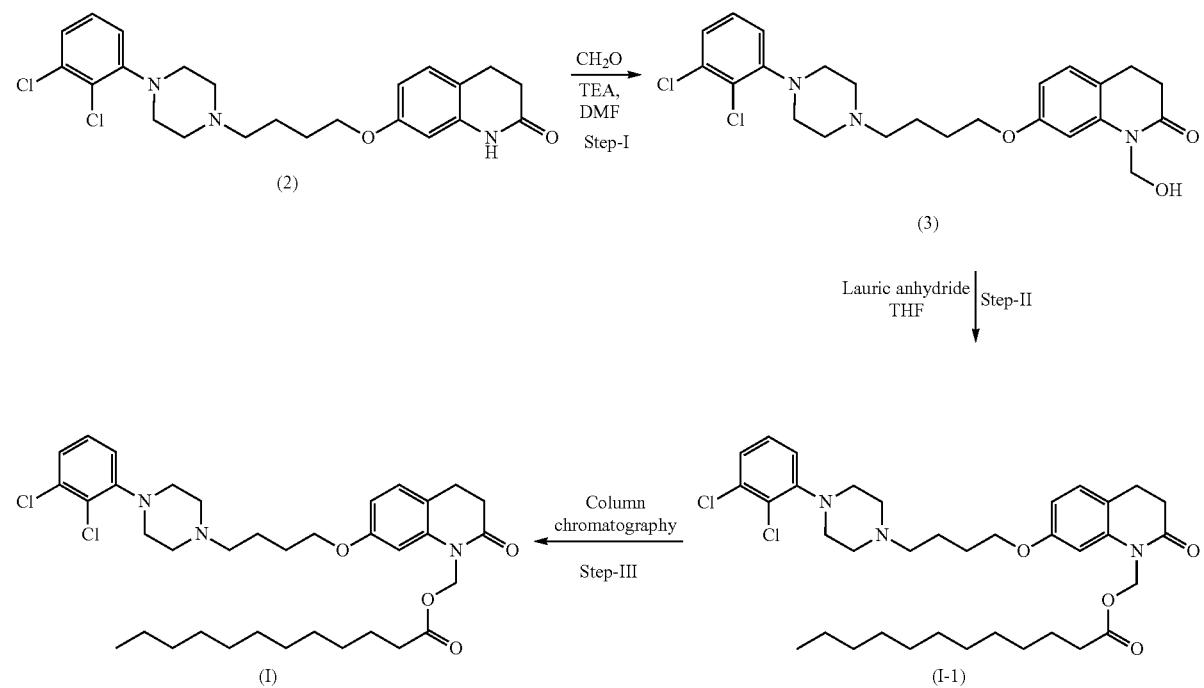

In Step-I: Conversion of Aripiprazole to N-hydroxymethyl Aripiprazole in the presence of formaldehyde and triethyl amine, which results 65% of N-hydroxymethyl aripiprazole and 25% of Aripirpazole. Therefore, there is a need of increasing yield of N-hydroxymethyl aripiprazole and less amount of Aripiprazole. Triethyl amine is used, which is not environmental friendly. Therefore, there is a need of using environmental friendly base.

In Step-II: Lauric anhydride is used for conversion of N-hydroxymethyl aripiprazole to Aripiprazole lauroxil, which is very expensive. Therefore, there is a need of using cheaper reagent.

In Step-III: column chromatography is used for the purification of Aripiprazole lauroxil, which is not feasible for commercial scale.

Hence, there is a need for an improved process for the preparation of Aripiprazole Lauroxil; which is simple, eco-friendly, inexpensive, reproducible and well suited for commercial scale.

SUMMARY

In one aspect, the present invention provides an improved process for the preparation of crude Aripiprazole Lauroxil of formula (I-1)

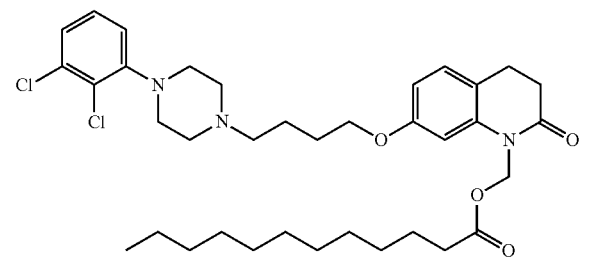

which comprises:

i) reacting Aripiprazole of formula (2)

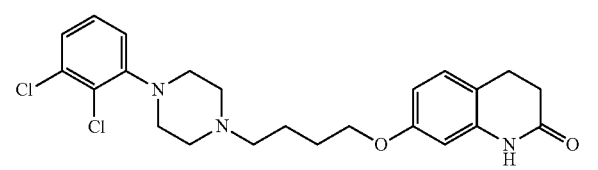

with formaldehyde and 4-dimethylaminopyridine in the presence of organic solvent to give N-hydroxymethyl Aripiprazole of formula (3);

ii) reacting N-hydroxymethyl Aripiprazole of formula (3)

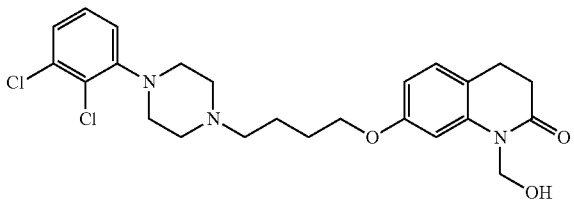

with Lauric acid in the presence of base, solvent and pivaloyl chloride to obtain crude Aripiprazole lauroxil of formula (I-1).

In another aspect, the present invention provides an improved process for the preparation of pure Aripiprazole Lauroxil of formula (I).

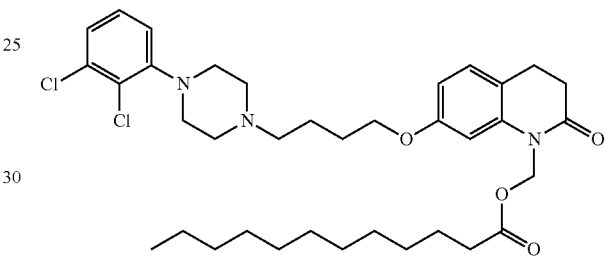

which comprises:

i) reacting Aripiprazole of formula (2)

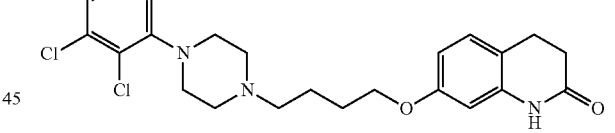

with formaldehyde and 4-dimethylaminopyridine in the presence of organic solvent to give N-hydroxymethyl Aripiprazole of formula (3);

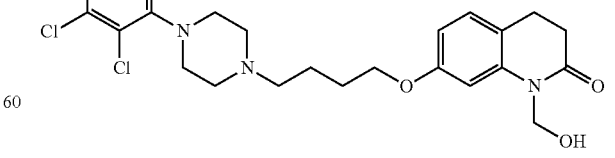

ii) reacting N-hydroxymethyl Aripiprazole of formula (3) with Lauric acid in the presence of base, solvent and pivaloyl chloride to obtain crude Aripiprazole Lauroxil of formula (I-1);

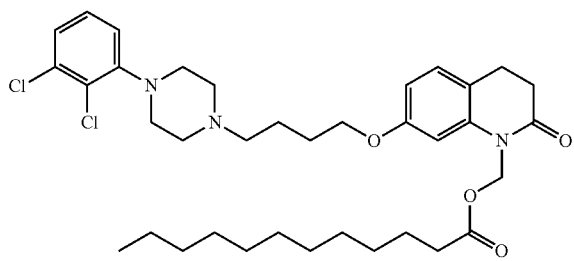

(I-1)

iii) purifying crude Aripiprazole Lauroxil of formula (I-1) with organic solvent or mixture of organic solvents to obtain pure Aripiprazole Lauroxil of formula (I).

In another aspect, the present invention provides Aripiprazole Lauroxil of formula (I) is free from impurities of formulae (4);

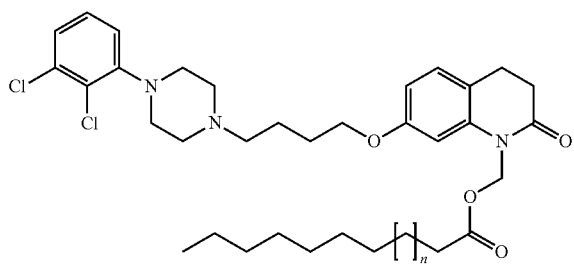

(4)

wherein, n=1, 2, 4 & 5

In further aspect, the present invention provides a pharmaceutical composition comprising:

(a) Aripiprazole Lauroxil of formula (I) having purity greater than 99.8%.

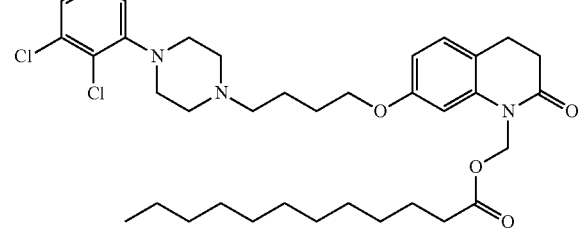

(I)

(b) sorbitan laurate;

(c) polysorbate 20; and (d) an aqueous vehicle wherein, the composition forms an aqueous, flocculated, injectable composition.

DETAILED DESCRIPTION

The main embodiment of present invention provides an improved process for the preparation of pure Aripiprazole Lauroxil of formula (I) as shown in the Scheme-2 given below;

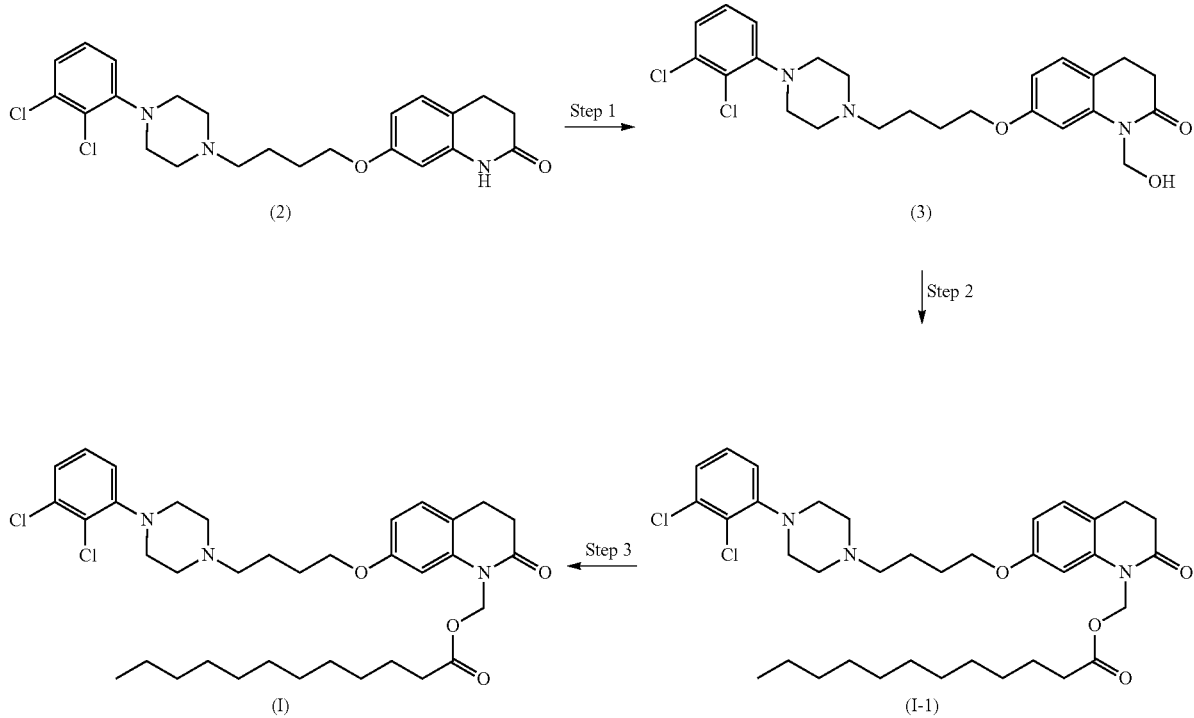

Scheme-2

Step 1:

Reacting Aripiprazole of formula (2) with formaldehyde and 4-dimethylaminopyridine in the presence of organic solvent to give N-hydroxymethyl Aripiprazole of formula (3); The solvent used is selected from the group consisting of dimethylformamide, dimethylacetamide, 1,4-dioxane, dimethylsulfoxide, lutidine or pyridine. Preferably, the solvent used is dimethylformamide. The reaction temperature may range from 20° C. to 40° C. and preferably at 25° C. to 35° C. The duration of the reaction may range from 5 hours to 7 hours, preferably for a period of 6 hours.

Step 2:

Reacting N-hydroxymethyl Aripiprazole of formula (3) with Lauric acid in the presence of base, solvent and pivaloyl chloride to give crude Aripiprazole Lauroxil of formula (I-1); The base used is selected from the group consisting of triethylamine, pyridine, diisopropylethylamine, potassium hydroxide, 1,8-Diazabicycloundec-7-ene (DBU) or 4-dimethylamino pyridine and mixture thereof. Preferably, the base used is mixture of triethylamine and 4-dimethylaminopyridine. The solvent used is selected from the group consisting of dichloromethane, dimethylformamide, chloroform, 1,4-dioxane, dimethylsulfoxide, lutidine or pyridine. Preferably, the solvent used is dichloromethane. The reaction temperature may range from 20° C. to 40° C. and preferably at a temperature of 25° C. to 35° C. The duration of the reaction may range from 4 hours to 6 hours, preferably for a period of 5 hours.

Step 3:

Purifying crude Aripiprazole Lauroxil of formula (I-1) with organic solvent or mixture of organic solvents to obtain pure Aripiprazole Lauroxil of formula (I).

The organic solvent or mixture of organic solvents are selected from the group consisting of acetone, propanone, butanone, methanol, ethanol, propanol, isopropanol, butanol, toluene, dimethyl formamide (DMF), dimethyl sulfoxide (DMSO), ethyl acetate or hexane. Preferably, the solvent used is dimethyl sulfoxide (DMSO).

In another embodiment, the present invention provides an improved process for the preparation of crude Aripiprazole Lauroxil of formula (I-1)

(I-1)

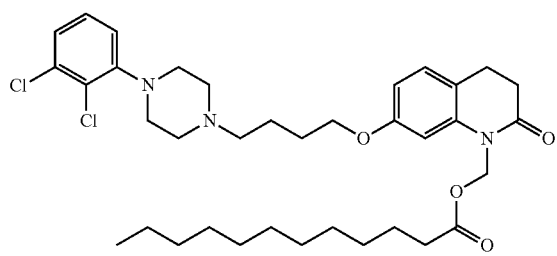

which comprises:
i) reacting N-hydroxymethyl Aripiprazole of formula (3)

(3)

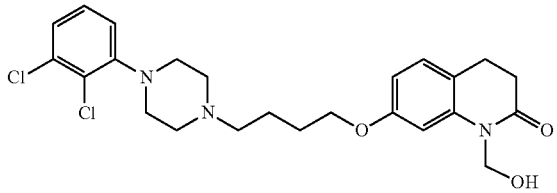

with Lauric acid in the presence of base, solvent and pivaloyl chloride to obtain crude Aripiprazole Lauroxil of formula (I-1).

In another embodiment, the present invention provides an improved process for the preparation of pure Aripiprazole Lauroxil of formula (I) from crude Aripiprazole Lauroxil of formula (I-1)

(I)

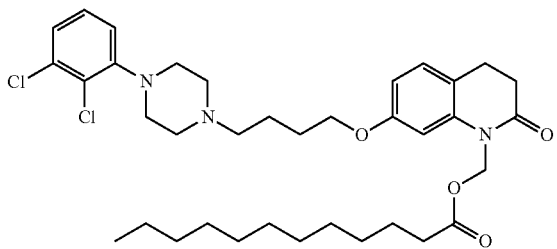

which comprises:
purifying crude Aripiprazole Lauroxil of formula (I-1) with organic solvent or mixture of organic solvents to obtain pure Aripiprazole Lauroxil of formula (I).

In another embodiment, the present invention provides an improved process for the preparation of pure Aripiprazole Lauroxil of formula (I)

(I)

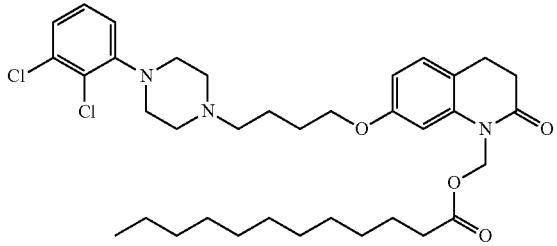

which comprises:
i) reacting Aripiprazole of formula (2)

(2)

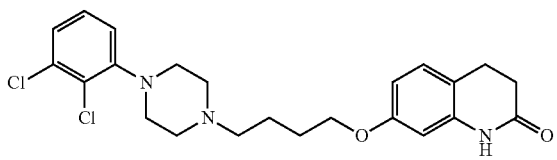

with formaldehyde and 4-dimethylaminopyridine in the presence of dimethylformamide to give N-hydroxymethyl Aripiprazole of formula (3);

(3)

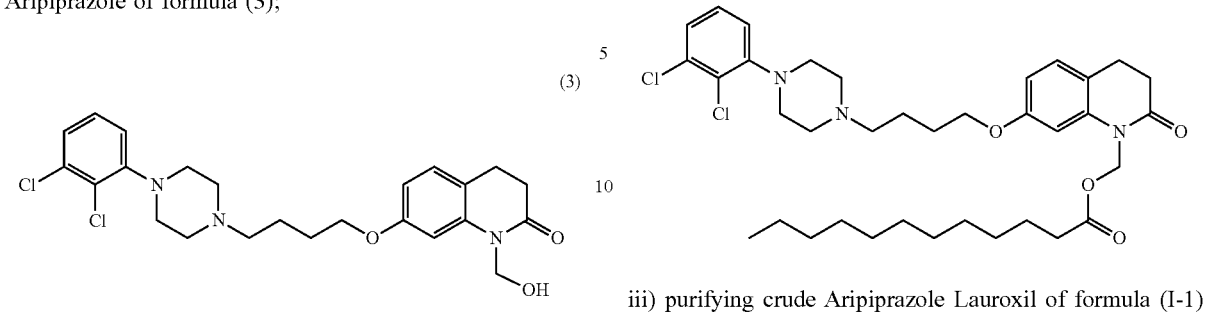

ii) reacting N-hydroxymethyl Aripiprazole of formula (3) with Lauric acid in dichloromethane in the presence of triethylamine, 4-dimethylaminopyridine and pivaloyl chloride to obtain crude Aripiprazole Lauroxil of formula (I-1);

(I-1)

iii) purifying crude Aripiprazole Lauroxil of formula (I-1) with dimethyl sulfoxide (DMSO) to obtain pure Aripiprazole Lauroxil of formula (I).

In further embodiment, alternative process for preparation of Aripiprazole Lauroxil of formula (I) is shown Scheme-3 given below:

Scheme-3

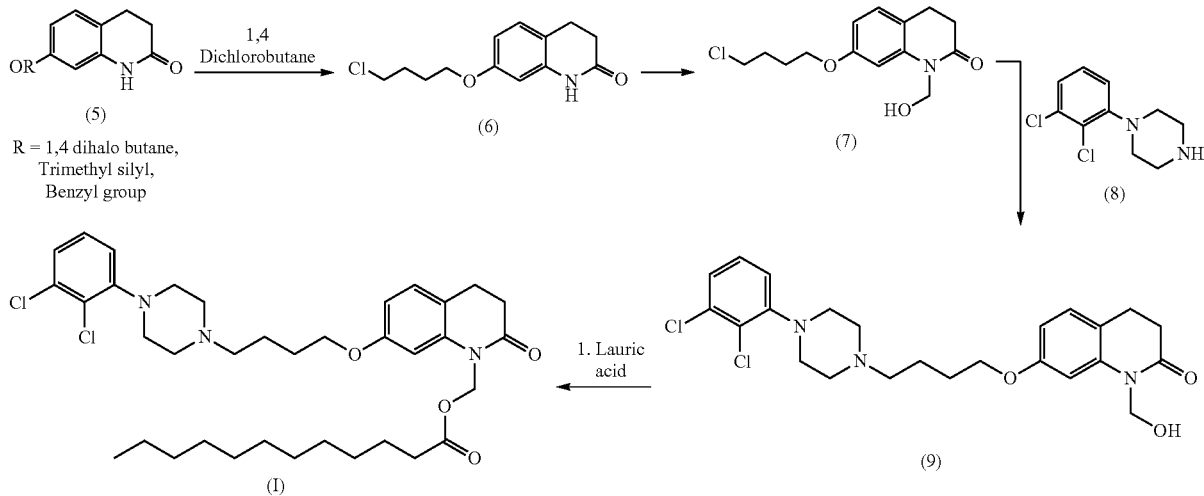

R = 1,4 dihalo butane,
Trimethyl silyl,
Benzyl group

Reaction of compound of formula (5) with 1,4-dichlorobutane to give compound of formula (6), followed by hydroxyl methylation using aldehyde or ketone to give compound of formula (7), which on further coupling with compound of formula (8) to give compound of formula (9), followed by reaction with Lauric acid in presence of base and solvent to give Aripiprazole Lauroxil of formula (I).

In further embodiment, another alternative process for preparation of Aripiprazole Lauroxil of formula (I) is shown Scheme-4 given below:

Scheme-4

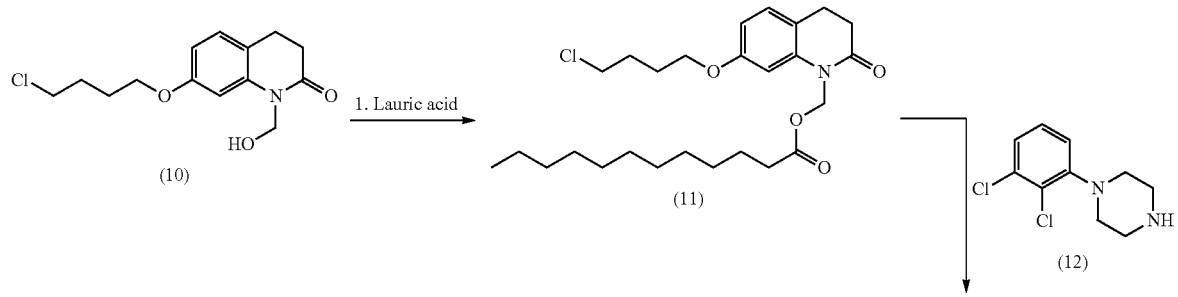

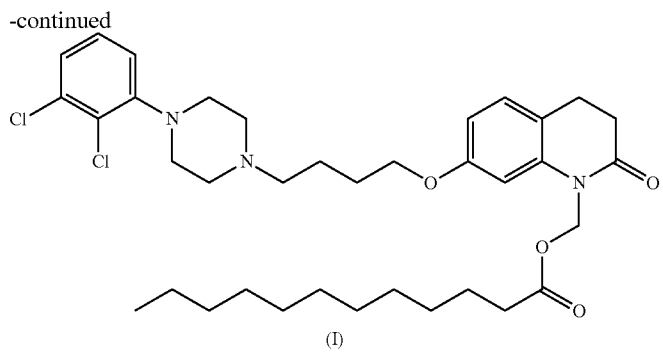

(I)

Reaction of compound of formula (10) with Lauric acid in presence of base and solvent to give compound of formula (11), followed by coupling with compound of formula (12) to obtain Aripiprazole Lauroxil of formula (I).

In further embodiment, another alternative process for preparation of Aripiprazole Lauroxil of formula (I) is shown Scheme-5 given below:

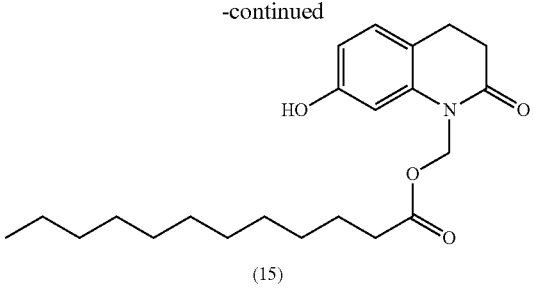

(15)

Scheme - 5

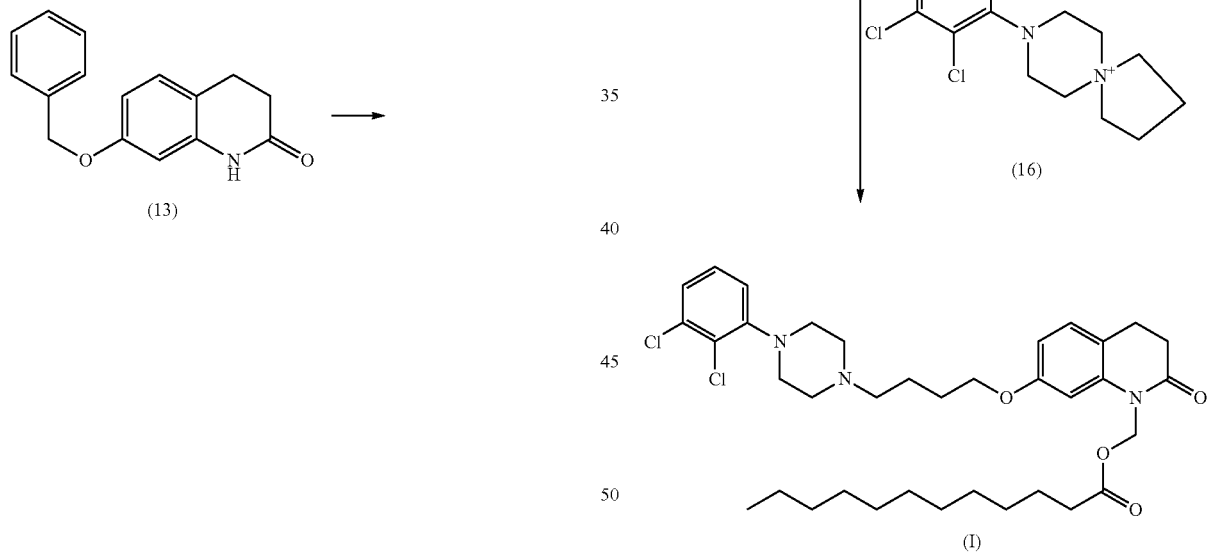

Reaction of compound of formula (13) with Lauric acid in presence base, solvent and aldehyde or ketone to give compound of formula (14), followed by deprotection to give compound of formula (15), which on further coupling with compound of formula (16) to obtain compound of formula (I).

Example-1: Preparation of Pure Lauric Acid

Commercially obtained Lauric acid was purified by using heptane, to control homologues acids with specifications limit less than 0.10%. Purity: >99.7%.

Example-2: Preparation of 7-(4-(4-(2, 3-dichlorophenyl) piperazin-1-yl) butoxide)-2-oxo-3, 4-dihydroquinolin-1(2H)-yl) methyl dodecanoate (Aripiprazole Lauroxil)

Step 1: Preparation of 7-(4-(4-(2, 3-dichlorophenyl) piperazin-1-yl) butoxy)-1-(hydroxymethyl)-3, 4-dihydroquinolin-2(1H)-one To the round bottom flask, charge Aripiprazole (100 grams, 223 m mole), dimethylformamide (DMF) (500 mL), formaldehyde (37% aqueous solution, 400 mL), 4-dimethylaminopyridine (5.4 grams, 44.64 mmol). The mixture was stirred at 25-35° C. for 6-10 hours. Slowly add 500 mL of water to the reaction mixture and filtered, dried under oven to give 7-(4-(4-(2,3-dichlorophenyl)piperazin-1-yl)butoxy)-1-(hydroxymethyl)-3,4-dihydroquinolin-2(1H)-one as a white solid. Yield: 87%; Purity: 92%.

$H^1$ NMR (CDCl$_3$): δ 1.57-1.79 (m, 4H), 2.37-2.42 (m, 2H), 2.48-2.55 (m, 5H), 2.71-2.76 (m, 2H), 2.78-2.98 (m, 5H), 3.87-3.94 (t, 2H), 5.22-5.32 (d, 2H), 5.86 (bs, 1H), 6.39-6.48 (m, 1H), 6.85-6.97 (m, 3H), 7.06-7.13 (d, 2H).

Step 2: Preparation of 7-(4-(4-(2, 3-dichlorophenyl) piperazin-1-yl) butoxide)-2-oxo-3, 4-dihydroquinolin-1(2H)-yl) methyl dodecanoate To a solution of Step-1 compound (50 grams, 104 mmol), charge Lauric acid (25.0 grams, 125 mmol) in dichloromethane (500 mL), triethylamine (17 grams, 167 mmol), 4-dimethylaminopyridine (2.5 grams, 20 mmol) and pivaloyl chloride (18.8 grams, 156 mmol). The reaction mixture was stirred for 5 hours at 25-30° C. The crude reaction mixture was washed with water (250 mL) followed by 10% sodium bi carbonate solution (200 mL), upon solvent evaporation under vacuum provided crude oil which on stirring with methanol (150 mL) results crude title compound as white solid (53 grams) which was further purified by using dimethyl sulfoxide (DMSO) to obtain pure compound as a white solid. Yield: 72%; Purity: >99%

$H^1$ NMR (CDCl$_3$): δ 0.88 (t, 3H), 1.25 (m, 20H), 1.64 (m, 2H), 1.72 (m, 2H), 1.84 (m, 2H), 2.36 (t, 2H), 2.49 (t, 2H), 2.68 (m, 6H), 2.86 (dd, 2H), 3.08 (m, 4H), 3.97 (t, 2H), 5.92 (brs, 2H), 6.59 (dd, 1H), 6.60 (s, 1H), 6.96 (dd, 1H), 7.07 (d, 1H), 7.14 (m, 2H).

Advantages of the Invention

1. The process of the present invention is simple and employs the use of readily available starting material thereby making the process economical and industrially viable.
2. The process involves the use of commercially available and cheaper reagents like Lauric acid unlike the use of the expensive reagents like Lauric anhydride used in prior art patent.
3. The process of the present invention avoids the use of lengthy column chromatography and involves the purification by crystallization techniques.

While the present disclosure has been illustrated and described with respect to a particular embodiment thereof, it should be appreciated by those of ordinary skill in the art that various modifications to this disclosure may be made without departing from the spirit and scope of the present disclosure.

We claim:

1. An improved process for the preparation of pure Aripiprazole Lauroxil of formula (I)

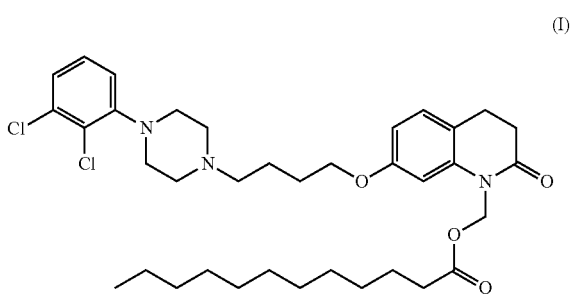 [SMILES: CCCCCCCCCCCC(=O)OCN1C(=O)CCc2ccc(OCCCCN3CCN(c4cccc(Cl)c4Cl)CC3)cc21]

which comprises;

i) reacting Aripiprazole of formula (2)

(2)

with formaldehyde and 4-dimethylaminopyridine in the presence of organic solvent, to give N-hydroxymethyl Aripiprazole of formula (3);

ii) reacting N-hydroxymethyl Aripiprazole of formula (3)

(3)

with Lauric acid in the presence of base, solvent and pivaloyl chloride to obtain crude Aripiprazole Lauroxil of formula (I-1); and

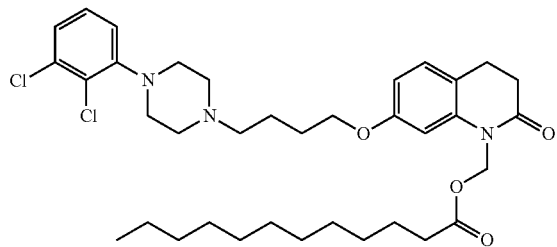

(I-1)

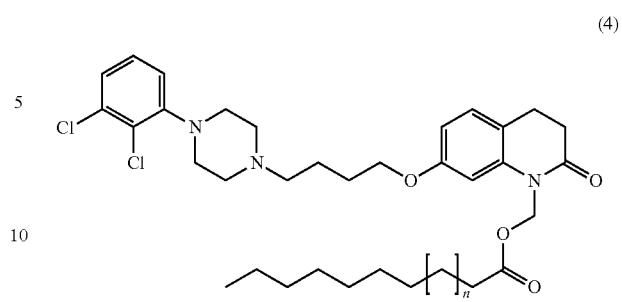

(4)

iii) purifying crude Aripiprazole Lauroxil of formula (I-1) with dimethylsulfoxide to obtain pure Aripiprazole Lauroxil of formula (I).

2. The process as claimed in claim 1, wherein the Lauric acid used in the preparation of crude Aripiprazole Lauroxil has a purity greater than 99.7% and the pure Aripiprazole Lauroxil obtained from crude Aripiprazole Lauroxil has a purity greater than 99.8%.

3. The process as claimed in claim 1, wherein said Aripirpazole Lauroxil of formula (I) obtained is free from impurities of formulae (4), wherein n is selected from 1, 2, 3, 4, and 5.

4. The process as claimed in claim 1, wherein the solvent used in step ii) is selected from the group consisting of dichloromethane, trichloromethane, dimethylformamide, 1,4-dioxane, dimethylsulfoxide, lutidine and chloroform.

5. The process as claimed in claim 1, wherein the base in step ii) is selected from the group consisting of triethylamine, diisopropylethylamine, 4-dimethylaminopyridine, potassium hydroxide, 1,8-diazabicycloundec-7-ene, pyridine and mixtures thereof.

* * * * *

UNITED STATES PATENT AND TRADEMARK OFFICE
CERTIFICATE OF CORRECTION

PATENT NO. : 10,815,216 B2
APPLICATION NO. : 16/469259
DATED : October 27, 2020
INVENTOR(S) : Ponnaiah Ravi et al.

Page 1 of 1

It is certified that error appears in the above-identified patent and that said Letters Patent is hereby corrected as shown below:

In the Claims

Claim 3, Column 15, Line 24, before "Lauroxil" delete "Aripirpazole" and insert -- Aripiprazole --.

Signed and Sealed this
Twentieth Day of April, 2021

Drew Hirshfeld
*Performing the Functions and Duties of the
Under Secretary of Commerce for Intellectual Property and
Director of the United States Patent and Trademark Office*